United States Patent [19]

Fischer et al.

[11] Patent Number: 4,940,805

[45] Date of Patent: Jul. 10, 1990

[54] PREPARATION OF 1,4-BUTANEDIOL OR TETRAHYDROFURAN OR BOTH

[75] Inventors: Rolf Fischer, Heidelberg; Hans-Juërgen Gosch, Bad Durkheim; Wolfgang Harder, Weinheim; Klaus-Dieter Malsch, Schifferstadt; Manfred Eggersdorfer, Frankenthal; Lothar Franz, Ludwigshafen; Horst Zimmermann, Heidelberg; Karl Brenner, Ludwigshafen; Klaus Halbritter, Mannheim, all of Fed. Rep. of Germany; Wolfgang Sauer, Everberg, Belgium; Hans-Juërgen Scheiper, Mutterstadt, Fed. Rep. of Germany

[73] Assignee: BASF Aktiengesellschaft, Ludwigshafen, Fed. Rep. of Germany

[21] Appl. No.: 230,015

[22] Filed: Aug. 8, 1988

[30] Foreign Application Priority Data

Aug. 8, 1987 [DE] Fed. Rep. of Germany ....... 3726509
Aug. 8, 1987 [DE] Fed. Rep. of Germany ....... 3726510

[51] Int. Cl.$^5$ ................. C07D 307/08; C07D 307/32; C07C 27/04
[52] U.S. Cl. .................................. 549/326; 549/508; 568/864
[58] Field of Search ................. 549/326, 508; 568/864

[56] References Cited

U.S. PATENT DOCUMENTS

| | | | |
|---|---|---|---|
| 4,652,685 | 3/1987 | Cawse et al. | 568/684 |
| 4,751,334 | 6/1988 | Turner et al. | 568/684 |
| 4,810,807 | 3/1989 | Budge et al. | 549/508 |

*Primary Examiner*—Richard L. Raymond
*Attorney, Agent, or Firm*—John H. Shurtleff

[57] ABSTRACT

Process for the preparation of 1,4-butanediol or tetrahydrofuran or both by the catalytic hydrogenation of maleic anhydride, succinic anhydride, maleic acid, succinic acid, fumaric acid, or the alkyl esters of these acids at temperatures of from 100° C. to 350° C. and pressures of from 50 bar to 350 bar over a catalyst containing cobalt as the active metal and one or both of the elements copper and phosphorus, if necessary in the presence of an aliphatic alcohol.

10 Claims, 1 Drawing Sheet

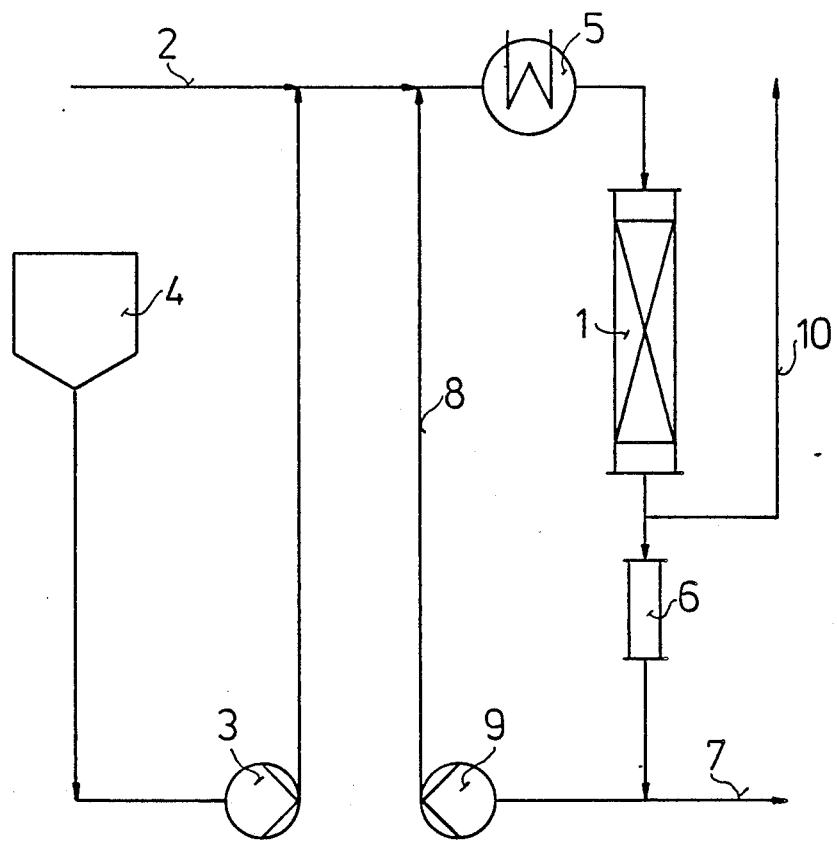

PREPARATION OF 1,4-BUTANEDIOL OR TETRAHYDROFURAN OR BOTH

The present invention relates to a process for the preparation of 1,4-butanediol or tetrahydrofuran or both by catalytic hydrogenation of maleic anhydride, succinic anhydride, maleic acid, succinic acid, fumaric acid, or the alkyl esters of these acids.

Tetrahydrofuran, 1,4-butanediol, and gamma-butyrolactone are valuable intermediates. Thus tetrahydrofuran and 1,4-butanediol are used inter alia for the manufacture of polyurethans, poly(butylene terephthalate), and polyterahydrofuran, and pyrrolidone is made from gamma-butyrolactone. Both tetrahydrofuran and gamma-butyrolactone are useful solvents.

It is well known that gamma-butyrolactone, tetrahydrofuran, and 1,4-butanediol are obtained by the catalytic hydrogenation of maleic anhydride. The hydrogenation takes place in stages, as described in U.S. Pat. No. 4,155,919, and efforts have been made to carry out the process in such a way as to influence the course of the reaction so that at least one of these reaction products is formed preferentially. In the known processes the product distribution usually favors either gamma-butyrolactone or both 1,4-butanediol and tetrahydrofuran.

gamma-Butyrolactone is obtained by the process described in U.S. Pat. No. 4,096,156, for instance, in which maleic acid, maleic anhydride, succinic anhydride, or fumaric acid or mixtures of these are hydrogenated in the presence of noble metals as catalysts. The disadvantages of this process are that it requires very expensive catalysts, and that the employment of these complex mixtures of noble metals entails a very laborious process for the recovery of the metals.

According to DE-OS No. 2 133 768 maleic anhydride is hydrogenated over a catalyst containing cobalt and either rhenium or molybdenum or both. In Example 3 of this patent application maleic anhydride is hydrogenated over cobalt and rhenium on a silica-alumina support, the mole ratio of Co to Re being 1:0.03; the product contains 6.9% of 1,4-butanediol, 22.3% of tetrahydrofuran, and 63.7% of gamma-butyrolactone. The catalysts described in DE-OS No. 21 33 768 have proved to be very sensitive to acids and other impurities.

U.S. Pat. No. 2,772,292 describes a single-stage process in which maleic anhydride is hydrogenated over Raney cobalt. According to Example 1 hydrogenation at a temperature of 275° C. under a pressure of about 800 bar gives 1,4-butanediol in 64% yield; tetrahydrofuran is formed in 11% yield.

The hydrogenation of maleic anhydride to 1,4-butanediol in the presence of aliphatic alcohols has also been carried out before. A single-stage process is described in DE-PS No. 2 845 905, but this has the disadvantage that it requires the use of a copper chromite catalyst that has to be made from toxic starting materials. The lifetimes attainable with catalysts of this kind are also not satisfactory for large-scale production.

A process for the preparation of 1,4-butanediol or tetrahydrofuran or both from the starting compounds named at the outset was required that did not suffer from these disadvantages, which lay in the catalysts. The catalyst in particular should contain only cheap non-precious metals, have a long life, be highly stable with respect to corrosion, and make it possible to achieve high yields of 1,4-butanediol, tetrahydrofuran, and the intermediate product gamma-butyrolactone. It was also desirable that all three compounds could be produced in proportions that could be varied.

In the novel process, which largely meets these demands, 1,4-butanediol or tetrahydrofuran or both are prepared by catalytic hydrogenation of compounds of the general formula

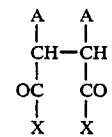

where either each A is a hydrogen atom or A & A together denote a single bond and either each X is a hydroxyl or alkoxy radical RO— (R is an alkyl radical of from 1 to 6 carbon atoms) or X & X together denote a ring oxygen atom —O——at temperatures of from 100° C. to 350° C. and under pressures of from 50 bar to 350 bar, the catalyst containing cobalt as the active metal and one or both of the elements copper and phosphorus.

Starting compounds of the general formula given include maleic acid, maleic anhydride, succinic acid, succinic anhydride, fumaric acid and alkyl maleates and succinates; maleic acid, maleic anhydride, and mixtures of the two are preferred. The starting substance can be inter alia in solution or molten when hydrogenated. The solution used may be, for example, a solution in which the mass fraction of maleic anhydride or maleic acid is from 5% to 60% and the solvent is water, gamma-butyrolactone, or an ether such as dioxan, tetrahydropyran, tetrahydrofuran, or diethyl ether. For instance, solutions of maleic anhydride in tetrahydrofuran are used in which the mass fraction of maleic anhydride is from 10% to 60%—preferably from 20% to 40% —, and the mass fraction of maleic acid in aqueous solutions is from 5% to 40%—preferably from 25% to 40%.

In this form of the process hydrogenation is carried out at a temperature in the range 150° C. to 350° C., preferably at from 170° C. to 250° C., under a pressure of from 50 bar to 350 bar, preferably from 250 bar to 300 bar. Batchwise hydrogenation is possible, but continuous hydrogenation is preferred.

In the novel process the required catalysts contain cobalt and one or both of the elements copper and phosphorus. The catalysts of choice contain cobalt and at least two of the elements copper, phosphorus, and molybdenum, and of these catalysts those that contain cobalt and at least three of the elements copper, phosphorus, molybdenum, and manganese are of particular industrial interest. In the case of the metallic elements the free metals or their oxides can be employed; phosphorus is conveniently introduced as phosphoric acid.

Suitable catalysts are, for example, those in which the mass fraction of cobalt in the active material is at least 40%, the fraction of copper is up to 20% (for instance from 5% to 18%), phosphoric acid up to 8% (for instance from 0.1% to 7%), and molybdenum up to 10% (for instance from 0.1% to 8%). Examples of such catalysts are those in which the mass fractions in the active material are from 40% to 60% of cobalt, from 13% to 17% of copper, from 0.5% to 5% of molybdenum (calculated as $MoO_3$), from 0% to 8% of manganese, and from 0.1% to 5% of phosphorus (calculated as $H_3PO_4$).

The catalysts can contain the usual inert materials, such as silicon dioxide, aluminum oxide, zeolites, titanium oxide, thorium oxide, magnesium oxide, pumice, rutile, zirconium oxide, or charcoal, for instance up to a mass fraction of 10%.

The catalyst usually contains the metal components as their oxides, and as a rule it is activated before use by treatment with hydrogen—most conveniently in the reactor itself—, which reduces the greater parts of the oxides to the free metals.

The useful lives of the catalysts are longer than seven months without loss of activity. The space-time yield is between 0.2 kg/l.h and 0.9 kg/l.h for molten starting materials and between 0.2 kg/l.h and 0.8 kg/l.h for starting materials in solution.

Generally the hydrogenation is carried out with a large excess of hydrogen, which can be recycled. Technically pure hydrogen is generally used, but the presence of inert gases such as nitrogen does not interfere with the course of the reactions.

Continuous production can be carried out by either the flooded-bed or the trickle-bed method. In batchwise hydrogenation a typical procedure is to charge a high-pressure autoclave with maleic anhydride dissolved in tetrahydrofuran and the catalyst, introduce hydrogen under pressure, and heat the mixture. When the reaction is completed the mixture is cooled, the catalyst is separated off, and the tetrahydrofuran, gamma-butyrolactone, and 1,4-butanediol are isolated by fractional distillation. If required it is also possible to post-hydrogenate the gamma-butyrolactone to 1,4-butanediol and tetrahydrofuran, then to cyclize the 1,4-butanediol in the usual way.

The novel process makes it possible to vary the mass fractions of the compounds in the mixture produced: thus the fraction of tetrahydrofuran can be from 20% to 100%, of gamma-butyrolactone up to 55%, of 1,4-butanediol up to 60%. The fraction of tetrahydrofuran is high when the reaction is carried out at high temperatures and/or with low catalyst loadings, while lower temperatures and/or high catalyst loadings favor the production of gamma-butyrolactone.

For example, when the catalyst loading is 0.4 kg/l.h reaction at a temperature of 260° C. gives a product in which the mass fraction of tetrahydrofuran is 50.8%, that of 1,4-butanediol 38.8%, and that of gamma-butyrolactone 4.6%; reaction at 210° C. gives a product in which the mass fraction of tetrahydrofuran is 29.5%, that of 1,4-butanediol 29.5%, and that of gamma-butyrolactone 34.1%. When the catalyst loading is reduced to 0.1 kg/l.h reaction at 220° C. gives a product in which the mass fraction of tetrahydrofuran is 23%, that of 1,4-butanediol 66%, and that of gamma-butyrolactone 2%; reaction at 170° C. gives a product in which the mass fraction of tetrahydrofuran is 5%, that of 1,4-butanediol 36%, and that of gamma-butyrolactone 58%.

In the novel process conversion of the starting compounds is quantitative, and the products are obtained in high yields; space-time yields are also high. Surprisingly, the catalyst is not observed to suffer from corrosion effects or deactivation, either when molten maleic anhydride or when aqueous solutions of maleic acid are employed. Side products are formed to only a very slight extent, and even the formation of pitch-like substances of high molecular weight, usual when maleic anhydride is hydrogenated at temperatures above 300° C., is not observed.

In another advantageous embodiment of the invention hydrogenation is carried out in the presence of an aliphatic alcohol and a catalyst containing cobalt and at least one of the elements copper, phosphorus, and manganese. When the known processes for the hydrogenation of maleic anhydride over cobalt catalysts are considered, it is surprising that the selectivity for 1,4-butanediol is greater than 80% and that the overall selectivity for 1,4-butanediol, tetrahydrofuran, and gamma-butyrolactone is 98%. Depending on the reaction conditions and the catalyst, varying proportions of the valued products tetrahydrofuran and gamma-butyrolactone can be obtained in addition to 1,4-butanediol.

It is also possible to post-hydrogenate the gamma-butyrolactone that is formed to 1,4-butanediol and tetrahydrofuran.

The half-esters of maleic acid are formed as soon as maleic anhydride is dissolved in alcohols, even at low temperatures. The reactions of maleic anhydride with an alcohol and hydrogen can therefore be represented by the partial equations (a) and (b). The alcohol employed is re-formed in the hydrogenation reaction, so that one molecule of maleic anhydride effectively reacts with five molecules of hydrogen, giving one molecule of 1,4-butanediol and one molecule of water, as shown by the overall equation (c).

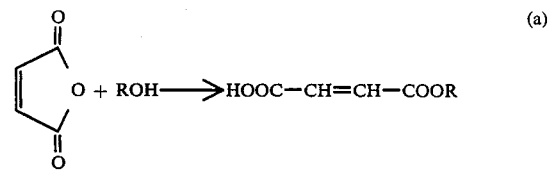

(a)

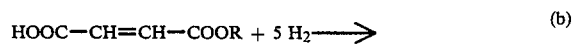

(b)

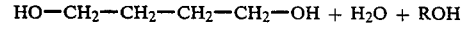

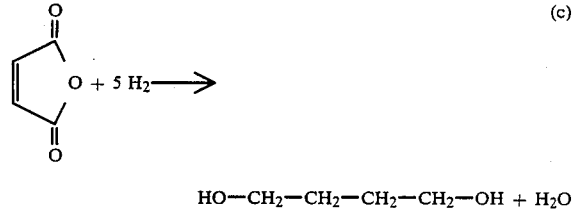

(c)

Solid, liquid, or gaseous maleic anhydride can be used. For the hydrogenation it is first dissolved in the alcohol, which can be done easily at room temperature or, for instance, temperatures between 30° C. and 70° C. It is particularly advantageous to absorb in an alcohol the maleic anhydride and water vapors contained in the gaseous mixture formed when butane or butenes are catalytically oxidized by air as described, for instance, in EP-PS No. 149 144. If this is done it is particularly easy to separate the water, although it is also possible to hydrogenate the mixture without removing the water first.

It is possible to start with succinic anhydride instead of maleic anhydride; in this case the working temperatures are from 30° C. to 100° C. It is also possible to employ esters or half-esters of maleic acid or succinic acid, such as the alkyl esters, for the hydrogenation. The alkyl esters are, for instance, those derived from aliphatic alkanols of from 1 to 6 carbon atoms, such as methanol, ethanol, isopropyl alcohol, propyl alcohol, hexanols, butyl alcohol, or isobutyl alcohol.

In this version of the process hydrogenation is carried out in the presence of an alcohol, for instance an aliphatic alcohol, particularly a monohydric alkanol of from 1 to 6 carbon atoms such as one of those named above. Butanols are especially preferred, because they make it possible to remove the water formed in the hydrogenation simply by azeotropic distillation. Other monohydric or polyhydric primary, secondary, or tertiary aliphatic or alicyclic alcohols are also suitable, but they offer no advantages because their boiling points are generally higher and there are more possible side reactions. The mole ratio of the maleic anhydride (or succinic anhydride, or esters and half-esters of maleic acid or succinic acid) to the alcohols is generally from 1:0.1 to 1:30, preferably from 1:0.5 to 1:20, especially from 1:1 to 1:10.

The temperatures at which hydrogenation in the presence of alcohols is carried out generally lie between 100° C. and 350° C., especially between 150° C. and 300° C. The working pressure is from 50 bar to 350 bar, especially from 100 bar to 300 bar. Hydrogenation is carried out batchwise or continuously, but especially continuously. Either the trickle-bed or flooded-bed method, with fixed-bed catalysts, is used, but especially the trickle-bed method. It is also possible to employ suspended catalyst. Both hydrogen and part of the product stream can be recycled in order to remove heat of reaction.

Both tubular and multitubular reactors—to name two examples—are suitable. The heat of reaction can be led off from tubular reactors by internal cooling, from multitubular reactors by external cooling. Suitable construction materials include normal stainless steels, for instance V-steels.

For this version of the process the catalysts used contain cobalt and at least one of the elements manganese, copper, and phosphorus. The catalysts of choice contain cobalt and at least two of the elements manganese, copper, phosphorus, and molybdenum, and of these catalysts those that contain cobalt and at least three of the elements manganese, copper, phosphorus, molybdenum, and sodium are of particular industrial interest. In the case of the metallic elements the free metals or their oxides—after reduction, by hydrogen for instance—can be employed; phosphorus is conveniently introduced as phosphoric acid.

Suitable catalysts are, for example, those in which the mass fraction of cobalt in the active material is at least 40%, the fraction of manganese is up to 10% (for instance from 3% to 7%), phosphoric acid up to 20% (for instance from 0.1% to 5%), and sodium up to 1% (for instance from 0.01% to 0.5%). Particularly good results are achieved, for example, with catalysts of this kind in which the active material also contains up to 30% of copper (for instance from 12% to 18%) and up to 5% of molybdenum (for instance from 1% to 4%).

The catalysts can be supported, but the employment of unsupported catalysts is preferable. Supported catalysts can be prepared conveniently by impregnating the support with an aqueous solution of the metal salts, once or several times, drying, and heating to convert the salts into the metal oxides. Before the catalysts are employed they are treated with hydrogen, which reduces the oxides almost completely to the free metals.

Suitable catalyst supports include silicon dioxide, aluminum oxide, titanium dioxide, active charcoal, silicates, and zeolites. Binders can be used if necessary in the preparation of the catalysts.

In the following examples the compositions of catalysts are given as mass fractions in the active material.

EXAMPLE 1

A trickle-bed reactor 3 m high and with an inside diameter of 16 mm was packed with cylindrical catalyst pellets 6 mm long and 3 mm in diameter. The active ingredients of the catalyst were

| $H_3PO_4$ 3.0% | CoO 64.2% (Co 50.5%) | CuO 18.5% (Cu 14.8%) |
|---|---|---|
| $Mn_3O_4$ 6.7% (Mn 4.8%) | $MoO_3$ 3.7% | |

An aqueous 40% solution of maleic acid and hydrogen under a pressure of 300 bar were fed to the head of the reactor. The make-up rate of fresh maleic acid solution was 200 g/h, and the recirculation rate was set at 9 l/h.

Three experiments were made at different temperatures. The corresponding yields of each product are tabulated below.

| | Yield/% (based on amount of maleic acid employed) | | | | | |
|---|---|---|---|---|---|---|
| t/°C. | THF | lactone | diol | propanol | butanol | residue |
| 260 | 50.8 | 4.6 | 38.8 | 0.9 | 2.6 | 1.8 |
| 230 | 45.4 | 18.6 | 30.3 | 0.1 | 2.3 | 2.5 |
| 210 | 29.5 | 34.1 | 29.6 | 0.1 | 1.3 | 1.2 |

EXAMPLE 2

The experiments of Example 1 were repeated with a different catalyst:

| $H_3PO_4$ 3.0% | CoO 64.2% (Co 50.5%) | CuO 18.5% (Cu 14.8%) |
|---|---|---|
| | $MoO_3$ 3.7% | |

| | Yield/% (based on amount of maleic acid employed) | | | | | |
|---|---|---|---|---|---|---|
| t/°C. | THF | lactone | diol | propanol | butanol | residue |
| 280 | 33.1 | 17.3 | 31.0 | 4.0 | 13.7 | 1.3 |
| 270 | 38.9 | 16.0 | 27.0 | 3.4 | 13.5 | 1.4 |
| 260 | 42.1 | 15.8 | 25.3 | 3.0 | 12.3 | 1.5 |

EXAMPLE 3

The experiments of Example 1 were again repeated with a different catalyst:

| $H_3PO_3$ 8.5% | CoO 62.0% (Co 48.7%) | CuO 17.8% (Cu 14.2%) |
|---|---|---|
| $Mn_3O_4$ 6.4% (Mn 4.5%) | $MoO_3$ 3.6% | |

| | Yield/% (based on amount of maleic acid employed) | | | | | |
|---|---|---|---|---|---|---|
| t/°C. | THF | lactone | diol | propanol | butanol | residue |
| 260 | 61.5 | 0.2 | 9.7 | 10.2 | 16.8 | 1.5 |
| 240 | 56.7 | 0.6 | 26.7 | 5.0 | 9.6 | 1.4 |
| 210 | 21.2 | 10.5 | 63.3 | 0.9 | 2.1 | 2.0 |

EXAMPLE 4

A reactor suitable for the flooded-bed method, 2 m high and with an inside diameter of 41 mm, was packed with cylindrical catalyst pellets 7 mm long and 4 mm in diameter. The composition of the catalyst was the same as in Example 1.

Molten maleic anhydride and hydrogen under a pressure of 300 bar were fed to the foot of the reactor. The make-up rate of fresh maleic anhydride was 0.7 l/h, and the recirculation rate was set at 20 l/h.

For a reactor temperature of 265° C. the yields were: 1,4-butanediol, 33%; tetrahydrofuran, 46%; gamma-butyrolactone, 11%; butanol, 4%; propanol, 1%.

EXAMPLE 5

Hydrogenation was carried out as described in Example 4, but the molten maleic anhydride was fed at the rate of 0.3 l/h and the rate of recirculation was set at 8 l/h.

For a reactor temperature of 245° C. the yields were: 1,4-butanediol, 46%; tetrahydrofuran, 37%; gamma-butyrolactone, 7%; butanol, 4%; propanol, 1%.

EXAMPLE 6

A trickle-bed reactor 10 m high and with an inside diameter of 41 mm was packed with catalyst pellets as used in Example 4.

Molten maleic anhydride and hydrogen under a pressure of 300 bar were fed to the head of the reactor. The make-up rate of fresh maleic anhydride was 7 l/h, and the recirculation rate was set at 40 l/h.

For a reactor temperature of 305° C. the yields were: 1,4-butanediol, 15%; tetrahydrofuran, 55%; gamma-butyrolactone, 25%; butanol, 1.5%; propanol, 0.5%.

EXAMPLE 7

Hydrogenation was carried out as described in Example 6, except that the temperature at the reactor inlet was 240° C. and at the outlet 280° C. The yields were: 1,4-butanediol, 15%; tetrahydrofuran, 55%; gamma-butyrolactone, 25%; butanol and propanol, 2%.

In another experiment the product stream emerging from the reactor outlet was led to a second reactor of the same dimensions as the first and packed with the same catalyst. Post-hydrogenation was carried out under a hydrogen pressure of 300 bar without the liquid's being recycled. The temperature at the reactor outlet was set at 260° C.

The yields were: 1,4-butanediol and tetrahydrofuran, 93%; gamma-butyrolactone, 1.5%; butanol, 2.5%; propanol, 0.4%.

EXAMPLE 8

The tubular reactor (1) of the recycle loop shown in the drawing, 2 m high and with an inside diameter of 16 mm, was packed with 612 g of catalyst pellets 4 mm in diameter. The active ingredients of the catalyst were

| H$_3$PO$_4$ 3.3% | CoO 63.4% | CuO 18.1% |
|---|---|---|
| | (Co 50.1%) | (Cu 14.5%) |
| Mn$_3$O$_4$ 6.8% | MoO$_3$ 2.1% | Na$_2$O 0.15% |
| (Mn 4.9%) | | (Na 0.1%) |

The reactor was heated to 100° C. and purged with nitrogen, then a mixture of nitrogen and hydrogen (volume fraction of hydrogen from 1% to 25%) was introduced via the inlet line (2) and passed through it. The temperature was raised at the rate of 20° C./h to 220° C. and then kept constant for 40 h.

After reduction of the catalyst, a mixture of maleic anhydride and 1-butanol in the mole ratio 1:2.5 fed from the tank (4) was introduced into the hydrogenation recycle loop at the rate of 50 g/h by means of the input pump (3); at the same time hydrogen entered via the line (2). The temperature was adjusted to from 200° C. to 230° C. by means of the heat exchanger (5).

The level control in the separator (6) ensured that the product stream left continuously via the outlet line (7) at a rate equal to the make-up rate. The recycle was returned via the line (8) by means of the circulatory pump (9). Off-gas was discharged through the outlet line (10).

Hydrogenation of the mixture was carried out for 3500 h under the following reactor conditions:

| Pressure | 200–250 bar |
|---|---|
| Temperature | 200–250° C. |
| Off-gas discharge rate | 50–100 l/h |
| Liquid recycle rate | 15 l/h |
| Superficial velocity | >80 m$^3$/m$^2$.h |

After 3500 h there was no noticeable falling-off in catalyst activity.

Quantitative gas-chromatographic analysis established that when the temperature was 230° C., the pressure 200 bar, and the rate of discharge of off-gas 100 l/h the results were as follows:

Conversion to 1,4-butanediol, gamma-butyrolactone, and tetrahydrofuran: 98%

| Selectivities: | 1,4-butanediol | 82% |
|---|---|---|
| | gamma-butyrolactone | 5% |
| | tetrahydrofuran | 11% |

EXAMPLE 9

Catalyst (100 ml, 186 g) was placed in a 1.5-l stirred autoclave. The active ingredients of the catalyst were

| H$_3$PO$_4$ 2.8% | CoO 92.3% |
|---|---|
| | (Co 50.5%) |
| Mn$_3$O$_4$ 5.3% | Na$_2$O 0.3% |
| (Mn 4.8%) | (Na 0.2%) |

The autoclave was purged with a stream of nitrogen (rate of flow about 300 l/h at s.t.p.) while being heated to a temperature of 220° C. Hydrogen was then introduced into the nitrogen stream; at first the volume fraction of hydrogen was 1%, then the value was slowly increased to 7%. The temperature was kept at 220° C. for 24 h, then the reactor was allowed to cool to room temperature.

The autoclave was charged with 880 g of a mixture of maleic anhydride and 1-butanol in the mole ratio 1:2.5, and hydrogenation was carried out under the following conditions:

| Temperature | 200° C. |
|---|---|
| Hydrogen pressure | 200 bar |
| Turbine speed | 2000 rev/min |

Liquid samples were taken from the autoclave after 21 h and 46 h and analyzed by gas chromatography and liquid chromatography. The results were as follows:

| Component | Mole fraction/% | |
|---|---|---|
| | 21 h | 46 h |
| Butyl hydrogen succinate | 3 | — |
| Dibutyl succinate | 9 | 1 |
| 1,4-Butanediol | 23 | 85 |
| gamma-Butyrolactone | 36 | 3 |
| Tetrahydrofuran | 3 | 3 |

Conversion to the required products 1,4-butanediol, gamma-butyrolactone, and tetrahydrofuran was 62% after 21 h and 91% after 46 h.

EXAMPLE 10

A tubular reactor 0.5 m high and with an internal diameter of 15 mm was packed with 104 g of catalyst of the same composition as that given in Example 8. The reactor was purged with nitrogen while being heated to a temperature of 290° C., then the nitrogen was steadily replaced by hydrogen over a period of 6 h. For a further 48 h pure hydrogen flowed, the temperature being held at from 300° C. to 310° C.

After the catalyst had been activated the temperature was adjusted to 250° C. and a mixture of maleic anhydride and 1-butanol in the mole ratio 1:2.5 was pumped into the reactor, together with hydrogen. The product left the reactor through a pressurizing valve connected to a condenser.

Quantitative gas-chromatographic analysis established that when the temperature was 250° C., the pressure 200 bar, and the rate of flow of hydrogen 60 l/h at s.t.p. the yields were as follows:

| 1,4-Butanediol | 62% |
|---|---|
| Tetrahydrofuran | 17% |
| gamma-Butyrolactone | 11% |

The yield of required products was thus 90%, and taking into account the esters of maleic acid and succinic acid, which could be recycled, the selectivity was 97%.

We claim:

1. In a process for the preparation of at least one of the compounds 1,4-butanediol, tetrahydrofuran and gamma-butyrolactone by catalytic hydrognenation of a compound of the formula

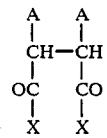

wherein each A is hydrogen or when taken together denote a single bond and each X is hydroxyl or alkoxy of from 1 to 6 carbon atoms or when taken together denote a ring oxygen atom —O—, at temperatures of from 100° C. to 350° C. and under pressures of from 50 bar to 350 bar, the improvement which comprises:

using a hydrogenation catalyst which contains cobalt and at least one of the elements copper, phosphorus and molybdenum.

2. A process as claimed in claim 1 wherein hydrogenation is carried out in the presence of an aliphatic alcohol.

3. A process as claimed in claim 1 wherein the catalyst contains cobalt and at least two of the elements copper, phosphorus, and molybdenum.

4. A process as claimed in claim 1 wherein the catalyst contains cobalt and at least two of the elements manganese, copper, phosphorus, and molybdenum.

5. A process as claimed in claim 1 wherein the catalyst contains cobalt and at least three of the elements manganese, copper, phosphorus, and molybdenum.

6. A process as claimed in claim 1 wherein the catalyst contains cobalt and at least three of the elements manganese, copper, phosphorus, molybdenum, and sodium.

7. A process as claimed in claim 1 wherein the mass fraction of cobalt in the active part of the catalyst is at least 40%.

8. A process as claimed in claim 1 wherein the mass fraction of cobalt in the active part of the catalyst is at least 40%, that of manganese from 0% up to 10%, that of phosphoric acid up to 20%, and that of sodium up to 1%.

9. A process as claimed in claim 1 wherein the mass fraction of cobalt in the active part of the catalyst is at least 40%, that of manganese from 0% up to 10%, that of copper up to 30%, that of molybdenum up to 5%, that of phosphoric acid up to 20%, and that of sodium up to 1%.

10. A process as claimed in claim 1 wherein the mass fraction of cobalt in the active part of the catalyst is from 40% to 60%, that of manganese up to 8%, that of copper from 13% to 17%, that of molybdenum from 0.5% to 5% (calculated as $MoO_3$), and that of phosphoric acid from 0.1% to 5% (calculated as $H_3PO_4$).

* * * * *

UNITED STATES PATENT AND TRADEMARK OFFICE
CERTIFICATE OF CORRECTION

PATENT NO. : 4,940,805

DATED : July 10, 1990

INVENTOR(S) : Fischer et al

It is certified that error appears in the above-identified patent and that said Letters Patent is hereby corrected as shown below:

In Claim 8 at line 38, delete the word "up".

In Claim 9 at line 43, delete the word "up".

In Claim 10 at line 49, delete the word "up" and substitute the words "from 0%".

Signed and Sealed this

Twenty-second Day of October, 1991

Attest:

HARRY F. MANBECK, JR.

*Attesting Officer*     *Commissioner of Patents and Trademarks*